(12) United States Patent
Rechner et al.

(10) Patent No.: US 8,741,873 B2
(45) Date of Patent: Jun. 3, 2014

(54) CONTROLS AND KIT FOR THROMBOCYTE ACTIVITY TESTS

(75) Inventors: Andreas Rechner, Marburg (DE); Norbert Zander, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 2 days.

(21) Appl. No.: 13/433,377

(22) Filed: Mar. 29, 2012

(65) Prior Publication Data

US 2012/0252044 A1   Oct. 4, 2012

(30) Foreign Application Priority Data

Apr. 4, 2011 (EP) ..................................... 11160934

(51) Int. Cl.
*A61K 31/727*   (2006.01)

(52) U.S. Cl.
USPC ............................................................ 514/56

(58) Field of Classification Search
USPC ........................................................... 514/56
See application file for complete search history.

(56) References Cited

U.S. PATENT DOCUMENTS

| | | | |
|---|---|---|---|
| 4,338,564 A | 7/1982 | Mundschenk | |
| 4,358,394 A | 11/1982 | Chastain, Jr. | |
| 6,103,705 A * | 8/2000 | Uzan et al. | 514/56 |
| 2006/0034809 A1 | 2/2006 | Ho | |
| 2007/0243632 A1 | 10/2007 | Coller | |

FOREIGN PATENT DOCUMENTS

| | | |
|---|---|---|
| EP | 1544621 | 6/2005 |
| EP | 1850134 A1 | 10/2007 |
| WO | WO 2005007868 | 1/2005 |
| WO | WO 2006020773 | 2/2006 |

OTHER PUBLICATIONS

European Search Report for EP11160934.3 dated Jun. 28, 2011, German.

* cited by examiner

*Primary Examiner* — Maryam Monshipouri
(74) *Attorney, Agent, or Firm* — King & Spalding L.L.P.

(57) ABSTRACT

The present invention is in the field of coagulation diagnostics and relates to a kit and method for preparing controls for use in test methods for determining thrombocyte function.

7 Claims, No Drawings

CONTROLS AND KIT FOR THROMBOCYTE ACTIVITY TESTS

This application claims the benefit of European Patent Application No. 11160934 filed on Apr. 4, 2011 which is incorporated by reference herewith in its entirety.

The present invention is in the field of coagulation diagnostics and relates to a kit and method for preparing controls for use in test methods for determining thrombocyte function.

Physiological processes which, firstly, ensure the fluidity of the blood in the vascular system and, secondly, make sure extravascular blood loss is avoided through the formation of blood clots are covered by the term hemostasis. The regulation of hemostasis involves a multiplicity of protein factors and also cellular components, for example thrombocytes (platelets). In the event of vascular injury, there is initially attachment of thrombocytes to the subendothelial collagen. This adhesion is mediated by adhesive proteins, such as von Willebrand factor (VWF). During the adhesion process, the thrombocytes are activated and release mediators from their granules, inducing the aggregation of further thrombocytes and intensification of activation. This achieves primary vascular wall occlusion (primary hemostasis), which is only stabilized by further reactions of the plasmatic coagulation system (secondary hemostasis). Dysregulation of these processes may lead to thrombophilia or bleeding diathesis and, depending on the severity, have life-threatening consequences.

In coagulation diagnostics, various methods and systems are known which make it possible to determine whether the blood of a patient can coagulate properly or whether a coagulation defect is present. In the event of a coagulation defect, it is often necessary to obtain more precise information about the cause of the defect present in order to be able to select the optimal therapeutic measures. An important subfunction of the coagulation system which can be tested specifically is primary hemostasis, which depends substantially on the functional efficiency of thrombocytes.

A known method for testing thrombocyte function is that of bleeding time determination. This is an in vivo global test which captures primary hemostasis. The bleeding time is determined by causing the patient a small cutting or stabbing injury and measuring the time for bleeding to stop. This is a difficult to standardize, rough test which is used especially in emergency situations to gain an overview of primary hemostasis. The intake of thrombocyte aggregation inhibitors leads to prolongation of bleeding time. A disadvantage of bleeding time determination is that, in the case of a normal bleeding time, a thrombocyte function defect cannot be ruled out.

In vitro methods permit substantially more sensitive detection of thrombocyte function defects. Typically, in these methods, aggregation of thrombocytes is induced in a whole blood sample or in a sample of platelet-rich plasma (PRP) by addition of an activator and the aggregation reaction is measured. The most commonly used activators to induce thrombocyte aggregation are: ADP (adenosine 5'-diphosphate), collagen, epinephrine (adrenaline), ristocetin and various combinations thereof and thrombin, TRAP (thrombin receptor activating protein) or serotonin.

In the prior art, various methods for testing thrombocyte function in vitro are known.

In the case of light transmission aggregometry, which is also referred to as Born platelet aggregation, the aggregation ability of thrombocytes in platelet-rich plasma is photometrically measured in the presence of aggregation-inducing substances in an aggregometer. Aggregate formation increases the light transmission of the PRP sample, and so by measuring light transmission it is possible to determine, for example, the rate of aggregate formation. Using light transmission aggregometry, it is also possible to capture therapeutic effects of thrombocyte aggregation inhibitors used medically. A disadvantage of light transmission aggregometry is that only platelet-rich plasma can be used as sample material. Platelet-rich plasma not only lacks important constituents of blood, for example red blood cells and white blood cells, but also requires time-consuming and error-prone sample preparation.

The VerifyNow® system (Accumetrics) is a further development of light transmission aggregometry which makes it possible to test thrombocyte function in whole blood samples. In this system, the aggregation reaction of thrombocytes is amplified by the addition of fibrinogen-coated microparticles.

Another test principle for determining thrombocyte function is what is known as the Platelet Function Analyzer system, or PFA system for short (PFA-100®, PFA-200, Siemens Healthcare Diagnostics Products GmbH, Marburg, Germany). Using the PFA system, primary hemostasis is measured in whole blood samples under flow conditions and hence in the presence of high shear forces.

To simulate the flow conditions and the shear forces which prevail in relatively small arterial blood vessels, a negative pressure of about −40 mbar is generated in a PFA measuring cell inserted into a PFA analysis device, and the citrated whole blood, which is located in a sample reservoir, flows through a capillary which has a diameter of about 200 µm. The capillary opens into a measuring chamber which is closed off by a partition element, for example a membrane, which contains a central capillary aperture through which the blood flows owing to the negative pressure. In most cases, the membrane, at least in the region around the aperture, contains one or more activators which induce thrombocyte aggregation, and so the blood which flows past comes into contact with the aggregation-inducing substances in the region of the aperture. The induced adhesion and aggregation of the thrombocytes results, in the region of the aperture, in the formation of a platelet plug (thrombus) which closes the membrane aperture and stops the blood flow. In this system, the time to closure of the membrane aperture is measured. This "closure time" correlates with the functional efficiency of the thrombocytes. The measuring cells typically used are equipped with a membrane coated with collagen (Col) and additionally either ADP or epinephrine (Epi). Other measuring cells which are especially suitable for determining antithrombotics from the group of the P2Y(12) antagonists, for example clopidogrel, have a membrane which contains ADP and prostaglandin E1 (EP-A1-1850134).

Another test principle for determining thrombocyte function is the Multiplate® system (Verum Diagnostica GmbH, Munich, Germany). Using the Multiplate system, primary hemostasis is measured in whole blood samples on the basis of impedance aggregometry. For this purpose, two sensor units, which each consist of two parallel sensor wires and which are arranged in a special measuring cell, are dipped into the whole blood sample. The addition of thrombocyte activators, for example ADP, collagen or arachidonic acid, induces the aggregation of the thrombocytes. The thrombocytes attach to the surface of the sensor wires, increasing the electrical resistance between the sensor wires. The measured increase in electrical resistance correlates with thrombocyte function.

It has hitherto not been possible to prepare fit-for-purpose and long-term stable control or standard material useful as control or standard in thrombocyte function tests in whole blood.

U.S. Pat. No. 4,338,564 and U.S. Pat. No. 4,358,394 describe methods for preparing hematological control materials which are suitable for use in cytometry because these preparations guarantee in particular the number, shape and size of the blood cells. However, these preparations are not suitable for testing thrombocyte function because the cells are treated with fixatives and other cell membrane-altering substances.

It is therefore an object of the present invention to provide control material for whole blood thrombocyte function tests.

The object is achieved by providing a storable kit which enables the user of a thrombocyte function test to prepare standardized controls in a simple manner.

The invention therefore provides a kit for preparing controls for a method for determining thrombocyte function, wherein the kit contains at least one first lyophilisate for preparing a first control having normal thrombocyte function and a second lyophilisate for preparing a second control having abnormally reduced thrombocyte function.

To prepare the controls, each lyophilisate is dissolved in whole blood which exhibits normal thrombocyte function.

Each lyophilisate of a kit according to the invention contains at least one buffer substance for maintaining a physiological pH and at least one auxiliary substance for lyophilization.

The physiological pH of blood is typically between about 7.35 and 7.45. Preferred buffer substances for maintaining a physiological pH are HEPES (2-[4-(2-hydroxyethyl)piperazin-1-yl]ethanesulfonic acid), PBS (phosphate-buffered saline), OVB (Owren's Veronal buffer), MES (2-(N-morpholino)ethanesulfonic acid), PIPES (piperazine-N,N'-bis(2-ethanesulfonic acid)), TAPS(N-[tris(hydroxymethyl)methyl]-3-aminopropanesulfonic acid), CHES (2-(cyclohexylamino)ethanesulfonic acid), CAPS(N-cyclohexyl-3-aminopropanesulfonic acid), Tris (tris(hydroxymethyl)aminomethane) or MOPS (3-(N-morpholino)propanesulfonic acid).

Preferred auxiliary substances for lyophilization are substances from the group of disaccharides, including sucrose, lactose, trehalose and maltose, and from the group of alcohols, preferably polyethylene glycol, mannitol and sorbitol. These substances have a cryoprotective or lyoprotective effect, i.e., they protect other constituents of the preparation during freezing and freeze-drying.

The lyophilisate for preparing a control having normal thrombocyte function is free of substances which affect thrombocyte function.

A lyophilisate for preparing a control having abnormally reduced thrombocyte function contains in addition at least one direct inhibitor of thrombocyte aggregation. A direct inhibitor of thrombocyte aggregation is to be understood as meaning a substance which has a direct effect on thrombocyte function, for example by blocking thrombocytic ADP receptors, inhibiting thrombocytic cyclooxygenase (COX) or blocking thrombocytic GP IIb/IIIa receptors. Direct inhibitors of thrombocyte aggregation must be distinguished from anticoagulants, which develop their coagulation-inhibiting effect by inhibiting plasmatic coagulation factors, such as thrombin or factor Xa, and may as a result have an indirect effect on thrombocyte function. In contrast to anticoagulants, direct inhibitors of thrombocyte aggregation do not, for example, prolong coagulation time in a coagulation test in plasma.

Suitable direct inhibitors of thrombocyte aggregation are, for example, tirofiban, abciximab, eptifibatide, acetylsalicylic acid, MRS 2395, AR-C66096, cangrelor, ticagrelor, cilostazol, dipyridamole, prostaglandin E1 (PGE1), prostacyclin, iloprost, cicaprost, forskolin, 2-MeSAMP (2-methylthioadenosine 5'-monophosphate), C1330-7 (N-1-(6-ethoxy-1,3-benzothiazol-2-yl-2-(7-ethoxy-4-hydroxy-2,2-dioxo-2H-2-6benzo[4,5][1,3]thiazolo[2,3-c][1,2,4]thiadiazin-3-yl)-2-oxo-1-ethanesulfonamide), MRS 2179 (2'-deoxy-N-6-methyladenosine 3',5'-diphosphate diammonium salt), MRS 2279 ((N)-methanocarba-N6-methyl-2-chloro-2'-deoxyadenosine 3',5'-bisphosphate), MRS 2500 (2-iodo-N6-methyl-(N)-methanocarba-2'-deoxyadenosine 3',5'-bisphosphate), A2P5P (adenosine 2',5'-bisphosphate), A3P5P (adenosine 3',5'-bisphosphate) and A3P5PS (adenosine 3'-phosphate 5'-phosphosulfate).

A lyophilisate for preparing a control having abnormally reduced thrombocyte function contains at least one direct inhibitor of thrombocyte aggregation in such an amount that a control is obtainable which preferably exhibits thrombocyte function of about 50% to about 80%, particularly preferably about 70%, of normal thrombocyte function.

A preferred kit contains a plurality of different lyophilisates for preparing controls having abnormally reduced thrombocyte function. These different lyophilisates may contain the same direct inhibitor of thrombocyte aggregation, but in different amounts. Alternatively, the lyophilisates may contain different direct inhibitors of thrombocyte aggregation.

A particularly preferred test kit contains lyophilisates which additionally contain normal human plasma. This has the advantage that there is compensation for any deficiencies in plasma constituents in the whole blood sample in which the lyophilisate is dissolved when preparing the control material. Low concentrations of certain plasma constituents, for example low concentrations of von Willebrand factor (VWF), may affect thrombocyte activity determination. The addition of said constituents in the form of normal human plasma ensures a minimum concentration of all plasmatic constituents, achieving stabilization of thrombocyte function in a control and hence improved standardization of test results. A lyophilisate of a test kit according to the invention preferably contains normal human plasma in such an amount that a control is obtainable which, after dissolution in whole blood, contains from about 2% to about 20% by volume of normal human plasma.

A further particularly preferred test kit contains lyophilisates which additionally contain isolated human von Willebrand factor (VWF). This has the advantage that there is compensation for any deficiencies in VWF in the whole blood sample in which the lyophilisate is dissolved when preparing the control material. This brings about stabilization of thrombocyte function in a control and hence improved standardization of test results. A lyophilisate of a test kit according to the invention preferably contains von Willebrand factor, preferably isolated human von Willebrand factor, in such an amount that a control is obtainable which, after dissolution in whole blood, contains from about 0.1 to about 10 IU/ml VWF, particularly preferably from 0.1 to about 1.0 IU/ml VWF, very particularly preferably from 0.1 to about 0.5 IU/ml VWF.

The term "lyophilisate" comprises end products of freeze-drying.

To prepare the lyophilisates of a kit according to the invention, it is typical to first prepare aqueous solutions which contain the desired substances at the desired concentrations. The solutions are aliquoted into vessels, preferably glass vials, and subsequently freeze-dried. The anhydrous, pulverulent residues are then sealed air-tight and can be stored for months or, if necessary, even years.

A test kit according to the invention preferably contains a plurality of vessels, preferably a plurality of glass or plastic vials, which contain the various lyophilisates sealed air-tight. The present invention further provides a method for preparing controls for a method for determining thrombocyte function. The controls are prepared by using a kit according to the invention which contains various lyophilisates. The various lyophilisates are dissolved in whole blood having normal thrombocyte function. Preferably, the whole blood is a fresh whole blood sample from a healthy donor. The whole blood is preferably anticoagulated with substance from the group consisting of citrate, hirudin, PPACK (D-phenylalanyl-L-prolyl-L-arginine chloromethyl ketone), BAPA (benzylsulfonyl-D-Arg-Pro-4-amidinobenzylamide) and heparin.

Preparation of the controls by dissolving the lyophilisates in whole blood is preferably not done until it is done by the user of a method for determining thrombocyte function.

EXAMPLES

The following exemplary embodiments serve to illustrate the invention and are not to be understood as limiting.

Example 1

Preparation of a Test Kit According to the Invention and Preparation of Controls for a Method for Determining Thrombocyte Function A test kit was prepared for preparing controls which are suitable for, inter alia, use in thrombocyte function tests according to the test principle of what is known as the Platelet Function Analyzer system (PFA-100®, PFA-200, Siemens Healthcare Diagnostics Products GmbH, Marburg, Germany).

Using the PFA system, primary hemostasis is measured in whole blood samples under flow conditions and hence in the presence of high shear forces. As a measure of thrombocyte function, in this system, the time to closure of a membrane aperture in a special measuring cell is measured (closure time). Measuring cells having different membrane types permit the determination of different functions of thrombocytes. The measuring cells used are provided with a membrane which has a collagen (Col) and ADP coating (Col/ADP), or which has a collagen (Col) and epinephrine (Epi) coating (Col/Epi), or which has an ADP and prostaglandin E1 coating (INNOVANCE® PFA P2Y).

It was intended to prepare a control which provides normal thrombocyte function with all three measuring cell types (normal control, level 1). In addition, it was intended to prepare a control which provides abnormally reduced thrombocyte function with all three measuring cell types (abnormal control, level 2). In addition, it was intended to prepare a control which provides abnormally reduced thrombocyte function only with Col/Epi measuring cells, but normal thrombocyte function with the other two measuring cell types (abnormal control Col/Epi, level 2). In addition, it was intended to prepare a control which provides abnormally reduced thrombocyte function only with INNOVANCE® PFA P2Y measuring cells, but normal thrombocyte function with the other two measuring cell types (abnormal control P2Y, level 2).

The desired thrombocyte functions of the various controls are summarized in table 1.

TABLE 1

Thrombocyte functions of the various controls

| PFA measuring cell | Normal control (level 1) | Abnormal control (level 2) | Abnormal control Col/Epi (level 2) | Abnormal control P2Y (level 2) |
| --- | --- | --- | --- | --- |
| Col/Epi | Normal | Abnormal | Abnormal | Normal |
| Col/ADP | Normal | Abnormal | Normal | Normal |
| INNOVANCE PFA P2Y | Normal | Abnormal | Normal | Abnormal |

Table 2 lists the substances which were used to prepare the lyophilisates. Firstly, stock solutions were prepared in distilled water at the concentrations indicated.

TABLE 2

Stock solutions of the substances used

| Substance | Stock solution concentration |
| --- | --- |
| HEPES | 238 g/mol |
| D-Mannitol | 182 g/mol |
| Acetylsalicylic acid (ASA) | 2.5 g/L |
| Tirofiban hydrochloride | 10 mg/mL |
| Prostaglandin E1 | 5 mg/mL |
| AR-C 66096 | 10 mM |

For each control, defined amounts of the stock solutions of the desired substances were pipetted into a glass vial (GW 5). The amount of stock solution to be pipetted was calculated such that a desired final concentration of the substances was present in the ready-prepared control. It was intended to prepare the controls by addition of a volume of, in each case, 2 mL of whole blood. The final concentrations of the substances in the various completed controls are summarized in table 3.

The liquid mixtures in the GW 5 vials were subsequently freeze-dried in a freeze-drying unit according to the following program: four hours freezing at −40° C. under 40% vacuum, then 8 hours drying at +20° C.

TABLE 3

Final concentration of the substances in 2 mL of whole blood

| | Normal control (level 1) | Abnormal control (level 2) | Abnormal control Col/Epi (level 2) | Abnormal control P2Y (level 2) |
| --- | --- | --- | --- | --- |
| Thrombocyte inhibitor | — | 0.1 µg/ml tirofiban | 10 nM PGE1 + 50 µM ASA | 200 nM AR-C66096 |
| Buffer | 5 mM HEPES | 5 mM HEPES | 5 mM HEPES | 5 mM HEPES |
| Auxiliary substances | 0.001% mannitol | 0.001% mannitol | 0.001% mannitol | 0.001% mannitol |

The lyophilisates of the controls described in table 3 were dissolved at room temperature for about 10 min in, in each case, 2 mL of citrated whole blood from a healthy blood donor.

Example 2

Use of Controls Prepared According to the Invention in a Method for Determining Thrombocyte Function in the PFA System The thrombocyte function of the controls prepared according to example 1 was measured in duplicate in a PFA analyzer with all three or with individual PFA measuring cells. Concurrently, the same whole blood samples which had been used to dissolve the lyophilisates were measured in their native state (i.e., with no addition of lyophilisates).

For the three different measuring cell types, cut-offs for the closure time (in seconds) which permit differentiation between normal thrombocyte function and abnormally reduced thrombocyte function had been determined beforehand. Samples having abnormally reduced thrombocyte function exhibit a prolonged closure time which is above the cut-off. The cut-offs for the various measuring cell types are summarized in table 4.

TABLE 4

Cut-offs for the three PFA measuring cell types

|  | Col/Epi | Col/ADP | INNOVANCE PFA P2Y |
|---|---|---|---|
| Cut-off | 165 s | 119 s | 106 s |

Normal Control (Level 1) (HEPES+Mannitol)

The normal control (level 1), which had been prepared by dissolving lyophilized HEPES and mannitol in whole blood, exhibits with all three measuring cell types slightly prolonged but normal closure times relative to native whole blood samples. Table 5 shows the average closure times of native whole blood samples compared to the average closure times of a normal control (level 1) in the various measuring cell types (aliquoted whole blood samples from a total of 14 healthy donors).

TABLE 5

Average closure times of the normal control (level 1)

| Measuring cell | Cut-off | Native whole blood | Normal control (level 1) |
|---|---|---|---|
| Col/Epi | 165 s | 99 s | 112 s |
| Col/ADP | 119 s | 85 s | 90 s |
| INNOVANCE PFA P2Y | 106 s | 64 s | 74 s |

Abnormal Control (Level 2) (HEPES+Mannitol+Tirofiban)

Since tirofiban blocks the activated GP IIb/IIIa receptor of thrombocytes, it prevents the aggregation of thrombocytes irrespective of the mode of activation and of the measuring cell type. Initial tests were therefore carried out only with the most strongly activating measuring cell Col/ADP. The abnormal control (level 2), which had been prepared by dissolving lyophilized HEPES, mannitol and tirofiban in whole blood, exhibits with the measuring cell type Col/ADP distinctly prolonged, abnormal closure times relative to native whole blood samples and relative to normal controls (level 1), the closures times being above the cut-off. Table 6 shows the average closure times of native whole blood samples and of normal controls (level 1) compared to the average closure times of an abnormal control (level 2) in Col/ADP measuring cells (aliquoted whole blood samples from a total of 14 healthy donors).

TABLE 6

Average Col/ADP closure time of the abnormal control (level 2)

| Measuring cell | Cut-off | Native whole blood | Normal control (level 1) | Abnormal control (level 2) |
|---|---|---|---|---|
| Col/ADP | 119 s | 87 s | 93 s | 287 s |

Abnormal Control Col/Epi (Level 2) (HEPES+Mannitol+Acetylsalicylic Acid+Prostaglandin E1)

The Col/Epi-specific abnormal control Col/Epi (level 2), which had been prepared by dissolving lyophilized HEPES, mannitol, acetylsalicylic acid and PGE1 in whole blood, exhibits with the measuring cell type Col/Epi distinctly prolonged, abnormal closure times relative to native whole blood samples and relative to normal controls (level 1), the closure times being above the cut-off. Table 7 shows the average closure times of native whole blood samples and of normal controls (level 1) compared to the average closure times of an abnormal control Col/Epi (level 2) in Col/Epi measuring cells (aliquoted whole blood samples from a total of 10 healthy donors).

TABLE 7

Average Col/Epi closure time of the abnormal control Col/Epi (level 2)

| Measuring cell | Cut-off | Native whole blood | Normal control (level 2) | Abnormal control Col/Epi (level 2) |
|---|---|---|---|---|
| Col/Epi | 165 s | 106 s | 117 s | 279 s |

Abnormal Control P2Y (Level 2) (HEPES+Mannitol+AR-C66096)

The INNOVANCE PFA P2Y-specific abnormal control P2Y (level 2), which had been prepared by dissolving lyophilized HEPES, mannitol and AR-C66096 in whole blood, exhibits with the measuring cell type INNOVANCE PFA P2Y distinctly prolonged, abnormal closure times relative to native whole blood samples and relative to normal controls (level 1), the closure times being above the cut-off. Table 8 shows the average closure times of native whole blood samples and of normal controls (level 1) compared to the average closure times of an abnormal control P2Y (level 2) in INNOVANCE PFA P2Y measuring cells (aliquoted whole blood samples from a total of 4 healthy donors).

TABLE 8

Average INNOVANCE PFA P2Y closure time of the abnormal control P2Y (level 2)

| Measuring cell | Cut-off | Native whole blood | Normal control (level 2) | Abnormal control P2Y (level 2) |
|---|---|---|---|---|
| INNOVANCE PFA P2Y | 106 s | 79 s | 79 s | 300 s |

Table 9 shows the average closure times of native whole blood samples and of the normal and abnormal controls prepared therewith according to the invention, in the three different PFA measuring cell types (aliquoted whole blood samples from a total of 4 healthy donors). The controls prepared according to the invention exhibit the desired thrombocyte activities (compare with table 1).

TABLE 9

Average closure times of the four different
controls in the three different measuring cell types

| PFA measuring cell | Native whole blood | Normal control (level 1) | Abnormal control (level 2) | Abnormal control Col/Epi (level 2) | Abnormal control P2Y (level 2) |
|---|---|---|---|---|---|
| Col/Epi Cut-off: 165 s | 119 s | 133 s (normal) | 300 s (abnormal) | 282 s (abnormal) | 152 s (normal) |
| Col/ADP Cut-off: 119 s | 100 s | 108 s (normal) | 300 s (abnormal) | 109 s (normal) | 116 s (normal) |
| INNOVANCE PFA P2Y Cut-off: 106 s | 79 s | 79 s (normal) | 300 s (abnormal) | 90 s (normal) | 300 s (abnormal) |

The invention claimed is:

1. A kit for preparing controls for a method for determining thrombocyte function, wherein the kit contains the following components:
   a. a first lyophilisate suitable for preparing a first control having normal thrombocyte function, wherein the lyophilisate consists of the following components:
      a buffer substance capable of maintaining a physiological pH, and an auxiliary substance capable of providing a cryoprotective or lyoprotective effect during lyophilization; and
   b. a second lyophilisate suitable for preparing a second control having abnormally reduced thrombocyte function, wherein the lyophilisate contains at least the following components:
      a buffer substance capable of maintaining a physiological pH,
      an auxiliary substance capable of providing a cryoprotective or lyoprotective effect during lyophilization, and
      a direct inhibitor of thrombocyte aggregation.

2. The kit as claimed in claim 1, wherein each lyophilisate additionally contains normal human plasma.

3. The kit as claimed in claim 1, wherein the buffer substance for maintaining a physiological pH is selected from the group consisting of HEPES, PBS, OVB, MES, PIPES, TAPS, CHES, CAPS, Tris and MOPS.

4. The kit as claimed in claim 1, wherein the second lyophilisate contains a direct inhibitor of thrombocyte aggregation from the group consisting of tirofiban, abciximab, eptifibatide, acetylsalicylic acid, MRS 2395, AR-C66096, cangrelor, ticagrelor, cilostazol, dipyridamole, prostaglandin E1, prostacyclin, iloprost, cicaprost, forskolin, 2-MeSAMP, C1330-7, MRS 2179, MRS 2279, MRS 2500, A2P5P, A3P5P and A3P5PS.

5. The kit as claimed in claim 1, wherein the second lyophilisate contains a direct inhibitor of thrombocyte aggregation in such an amount that a control is obtainable which exhibits thrombocyte function of between about 50% and about 80% of normal thrombocyte function.

6. The kit as claimed in claim 1, wherein the second lyophilisate contains a direct inhibitor of thrombocyte aggregation in such an amount that a control is obtainable which exhibits thrombocyte function of about 70% of normal thrombocyte function.

7. A kit for preparing controls for a method for determining thrombocyte function, wherein the kit includes:
   a first lyophilisate that is dissolvable in whole blood to produce a first control having normal thrombocyte function, wherein the lyophilisate consists of:
      a buffer substance capable of maintaining a physiological pH, and
      an auxiliary substance capable of providing a cryoprotective or lyoprotective effect during lyophilization; and
   a second lyophilisate that is dissolvable in whole blood to produce a second control having abnormally reduced thrombocyte function, wherein the lyophilisate includes:
      a buffer substance capable of maintaining a physiological pH,
      an auxiliary substance capable of providing a cryoprotective or lyoprotective effect during lyophilization, and
      a direct inhibitor of thrombocyte aggregation.

* * * * *